US00PP27097P2

(12) United States Plant Patent
Hartman

(10) Patent No.: US PP27,097 P2
(45) Date of Patent: Aug. 23, 2016

(54) ***CALADIUM* PLANT NAMED 'CAROUSEL'**

(50) Latin Name: *Caladium×hortulanum*
Varietal Denomination: Carousel

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 88 days.

(21) Appl. No.: 14/544,174

(22) Filed: Dec. 4, 2014

(51) Int. Cl.
*A01H 5/12* (2006.01)

(52) U.S. Cl.
USPC ..... Plt./373

(58) Field of Classification Search
USPC ..... Plt./373
See application file for complete search history.

*Primary Examiner* — June Hwu
(74) *Attorney, Agent, or Firm* — C. A. Whealy

(57) ABSTRACT

A new and distinct cultivar of *Caladium* plant named 'Carousel', characterized by its intermediate height; upright and uniform plant habit; vigorous growth habit and very rapid growth rate; fancy-type leaves with white-colored interveinal panels that are often and randomly blushed with light pink, red-colored venation and dark green-colored margins; and good landscape performance and sun tolerance.

4 Drawing Sheets

Botanical designation: *Caladium×hortulanum.*
Cultivar denomination: 'CAROUSEL'.

BACKGROUND OF THE INVENTION

The present invention relates to a new and distinct cultivar of *Caladium* plant, botanically known as *Caladium×hortulanum*, commercially referred to as a fancy leaf-type *Caladium* and hereinafter referred to by the name 'Carousel'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor on Apr. 15, 2007 in Avon Park, Fla. of *Caladium×hortulanum* 'White Christmas', not patented, as the female, or seed, parent with *Caladium×hortulanum* 'John Peed', not patented, as the male, or pollen, parent. The new *Caladium* plant was discovered and selected by the Inventor as a single plant within the progeny of the stated cross-pollination in a controlled outdoor nursery environment in Zolfo Springs, Fla. on Sep. 15, 2008.

Asexual reproduction of the new *Caladium* plant by 'chipping' the tubers (cutting the tuber into segments with each segment containing an axillary bud and tuber cortical tissue) in a controlled outdoor nursery environment in Zolfo Springs, Fla. since Apr. 15, 2009 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Carousel'. These characteristics in combination distinguish 'Carousel' as a new and distinct *Caladium* plant:

1. Intermediate in height; upright and uniform plant habit.
2. Vigorous growth habit and very rapid growth rate.
3. Fancy-type leaves with white-colored interveinal panels that are often and randomly blushed with light pink, red-colored venation and dark green-colored margins.
4. Good landscape performance and sun-tolerant.

Plants of the new *Caladium* differ primarily from plants of the female parent, 'White Christmas', in the following characteristics:

1. Plants of the new *Caladium* and 'White Christmas' differ in leaf color as leaves of plants of 'White Christmas' are dark green in color with white-colored interveinal panels and dark green-colored venation.
2. Plants of the new *Caladium* and 'White Christmas' differ in leaf petiole color as leaf petioles of plants of 'White Christmas' are green in color with close to black-colored stripes.

Plants of the new *Caladium* differ primarily from plants of the male parent, 'John Peed', in the following characteristics:

1. Plants of the new *Caladium* are more freely clumping and denser than plants of 'John Peed'.
2. Plants of the new *Caladium* are faster growing and produce finished plants about two to three weeks earlier than plants of 'John Peed'.
3. Plants of the new *Caladium* and 'John Peed' differ in leaf color as leaves of plants of 'John Peed' are dark green in color with red-colored centers and venation.
4. Plants of the *Caladium* and 'John Peed' differ in leaf petiole coloration as leaf petioles of plants of 'John Peed' are dark pink to dark green in color with close to black-colored stippling and streaks.

Plants of the new *Caladium* can be compared to plants of *Caladium×hortulanum* 'Tapestry', not patented. In side-by-side comparisons, plants of the new *Caladium* differed primarily from plants of 'Tapestry' in the following characteristics:

1. Plants of the new *Caladium* and 'Tapestry' differed in leaf color as leaves of plants of 'Tapestry' were olive green in color with white-colored interveinal panels tinged with pink and rose pink-colored primary veins.
2. Plants of the new *Caladium* and 'Tapestry' differed in leaf petiole color as leaf petioles of plants of 'Tapestry' were mostly pink to greenish pink with darker russet-colored stippling.

Plants of the new *Caladium* can also be compared to plants of *Caladium×hortulanum* 'Celebration', disclosed in U.S. Plant Pat. No. 23,993. In side-by-side comparisons, plants of the new *Caladium* differed primarily from plants of 'Celebration' in the following characteristics:

1. Plants of the new *Caladium* were more compact than plants of 'Celebration'.
2. Plants of the new *Caladium* were more freely clumping and denser than plants of 'Celebration'.
3. Plants of the new *Caladium* and 'Celebration' differed in leaf color as leaves of plants of 'Celebration' were dark green in color with white-colored interveinal panels and rose red-colored primary veins.
4. Leaf petioles of plants of the new *Caladium* were lighter in color than leaf petioles of 'Celebration'.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Carousel' in a container and grown in a shadehouse (tuber de-eyed).

The photograph at the top of the second sheet is a comparison view of typical potted plants of the male parent, 'John Peed' (left), 'Carousel' (center) and the female parent, 'White Christmas' (right).

The photograph at the bottom of the second sheet is a comparison view of typical potted plants of 'Celebration' (left), 'Carousel' (center) and 'Tapestry' (right).

The photograph at the top of the third sheet is a comparison view of typical plants of 'Carousel' grown in containers; the plant on the left has not had its tuber de-eyed and the plant on the right has had its tuber de-eyed prior to planting.

The photograph at the bottom of the third sheet is a close-up view of typical freshly-harvested tubers and roots of 'Carousel' plants.

The photograph at the top of the fourth sheet is a side perspective view of typical plants of 'Carousel' grown in an open field.

The photograph at the bottom of the fourth sheet is a close-up view of a typical inflorescence of 'Carousel'.

DETAILED BOTANICAL DESCRIPTION

The aforementioned photographs and following observations and measurements describe plants grown in 15-cm containers in a polypropylene-covered shadehouse (30% light reduction) in Avon Park, Fla. and plants grown in ground beds under full sunlight conditions in an outdoor nursery in Crewsville, Fla. The plants were grown under cultural practices typical of commercial shadehouse and outdoor nursery production. During the production of the shadehouse-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from about 10,000 to 12,000 foot-candles. Plants grown in the shadehouse were seven weeks old, and plants grown in the outdoor nursery were eight months old when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'Carousel'.

Parentage:

*Female, or seed, parent.*—*Caladium×hortulanum* 'White Christmas', not patented.

*Male, or pollen, parent.*—*Caladium×hortulanum* 'John Peed', not patented.

Propagation:

*Type*.—By "chipping" the tubers.

*Time to initiate roots, summer*.—About seven to ten days at temperatures about 32° C.

*Time to initiate roots, winter*.—About two to three weeks at temperatures about 24° C.

*Tuber description* (*outdoor nursery-grown plants*).—Appearance: Multi-segmented and somewhat flattened; individual segments elliptic in shape. Height: About 3.7 cm. Diameter: About 6.7 cm to 7.8 cm. Segment height: About 3.1 cm. Segment diameter: About 2.8 cm. Texture: Thick, starchy; somewhat brittle. Color: Epidermis, freshly-harvested: Close to 199B. Epidermis, dried: Close to 200A. Cortical tissue: Close to 8C to 8D. Axillary buds: Close to between 35D and 36A. Root description: Thick, fleshy contractile roots; color, close to 155C and 199C. Rooting habit: Dense.

Plant description:

*Plant type*.—Herbaceous perennial; suitable as a potted plant in containers 15-cm to 25-cm and suitable as a landscape plant in shaded and sunny areas.

*Plant and growth habit*.—Intermediate in height; upright and uniformly mounded plant habit; vigorous and dense growth habit; very rapid growth rate, potted plants in finished or saleable form in about six weeks after planting tubers; leaf petioles and leaves arise from one or more growing points on tubers; petioles mostly upright and leaning somewhat outwardly with development.

*Plant height, from soil level to top of foliar plane, shadehouse-grown potted plants*.—About 28 cm to 35 cm.

*Plant height, from soil level to top of inflorescences, shadehouse-grown potted plants*.—About 34.5 cm.

*Plant diameter or spread, shadehouse-grown potted plants*.—About 40 cm to 45 cm.

*Number of shoots per plant, shadehouse-grown potted plants, tubers not de-eyed*.—About three develop per #1 tuber.

*Number of shoots per plant, shadehouse-grown potted plants, tubers de-eyed*.—About three to five develop per #1 tuber.

*Cataphylls, shadehouse-grown potted plants*.—Length: About 4.5 cm to 7 cm. Width: About 7 mm to 11 mm. Shape: Wedge-shaped. Apex: Acuminate or cuspidate. Base: Sheathing the stem. Color, inner surface: Close to N155C; colors and patterns of the outside surface are visible on the inner surface. Color, outer surface: Close to 195C to 195D tinged with close to 147C to 147D and streaked and stippled with close to 200D; with development, color becoming closer to 200C.

Leaf description:

*Arrangement and type*.—Alternate; simple; fancy-type.

*Length, shadehouse-grown potted plants*.—About 17 cm to 22 cm.

*Width, shadehouse-grown potted plants, flattened*.—About 11 cm to 14 cm.

*Shape*.—Ovate.

*Apex*.—Acuminate to acute.

*Base*.—Sagittate to peltate.

*Margin*.—Entire; mostly flat with some broad undulations.

*Texture, upper and lower surfaces*.—Smooth to somewhat rugose, glabrous.

*Luster, upper surface*.—Dull sheen.

*Luster, lower surface*.—Glaucous, dull sheen.

*Venation pattern*.—Pinnate.

*Color, shadehouse-grown potted plants*.—Developing leaves, upper surface: Main color and towards margin: Close to 147A tinged with close to 146A. Interveinal panels: More white than close to 155C; small random areas, close to 155C tinged with close to 146D or close to 147B. Margin edge: Close to 187B. Basal notch: Close to 187B. Midrib and primary venation: Close to 53A and 187B. Developing leaves, lower surface: Main color and towards margin: Close to 191A and 191B. Interveinal panels: Close to 155C and close to 155C variably tinged with close to 186C; small areas, close to 147B. Margin edge: Close to 187B. Basel notch and proximal longitudinal line: Close to 187B. Midrib and proximal primary venation: Close to 194B tinged with close to 182B to 182C; adjacent to venation, close to 185C. Distal primary venation: Close to 194A to 194B; adjacent to venation, close to 185C. Fully expanded leaves, upper surface: Main color and towards margin: Close to 147B. Interveinal panels: Close to 155C variably tinged with close to 186D, 63C and/or 54C; areas surrounding venation, close to diffuse 147B with speckling, close to 155C; small random areas, close to 54B. Margin edge: Close to 187B. Basal notch: Close to 187B to 187C. Proximal longitudinal line: Close to 187B. Midrib: Close to 53A and 187B. Primary venation: Close to 187B. Fully expanded leaves, lower surface: Main color and towards margin: Close to 191A. Interveinal panels: Close to 155C variably tinged with close to 186D; small areas, close to 191C and close to 146B to 146C. Margin edge: Close to 187B. Basal notch and proximal longitudinal line: Close to 187B. Midrib: Close to 195B to 195C tinged with close to 182C; adjacent to venation, close to 185C to 185D. Distal primary venation: Close to 195A to 195B tinged with close to 181C to 181D; adjacent to venation, close to 185C to 185D.

*Petioles*.—Aspect: Initially upright and straight; with development, leaning outwardly; flexible. Length, shadehouse-grown potted plants: About 21.5 cm to 24 cm. Diameter, distal, shadehouse-grown potted plants: About 3.5 mm to 4 mm. Diameter, proximal, shadehouse-grown potted plants: About 9 mm. Texture: Smooth, glabrous; glaucous. Color, shadehouse-grown potted plants, Just below the leaf and petiole junction: Lighter than close to 181D tinged, stippled and streaked with close to 200D. Overall: Close to N170D and 181D variably tinged with close to 146C to 146D and striped, streaked, stippled and tessellated with close to 200D. Wing length, shadehouse-grown potted plants: About 5.5 cm to 7.2 cm. Wing diameter, shadehouse-grown potted plants: About 9 mm to 12 mm. Texture, inner and outer surfaces: Smooth, glabrous. Wing color, shadehouse-grown potted plants, inner surface: Close to N155C. Wing color, shadehouse-grown potted plants, outer surface: Close to 195C tinged with close to 147C and stippled, streaked, mottled and striped with close to 200D.

Inflorescence description: Inflorescences observed on seven week-old shadehouse-grown potted plants.

*Inflorescence arrangement*.—Upright hooded spathes surrounding a columnar spadix borne on a tall upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; sweet, jasmine-like with camphor note.

*Natural flowering season and flower longevity*.—Plants of the new *Caladium* typically flower during the spring in central Florida; early flowering habit, flowers develop about seven weeks after growth commences; inflorescences last about three days before fading; inflorescences persistent.

*Spathe*.—Length, overall: About 9.7 cm. Length, distal open portion: About 6 cm. Length, proximal closed portion: About 3.7 cm. Width, distal open portion: About 3.2 cm. Width, at constriction: About 1 cm. Width, proximal closed portion: About 2.9 cm. Shape: Obovate to elliptic. Apex: Acuminate tending towards cuspidate. Base: Obtuse. Margin: Entire. Texture, front and rear surfaces: Smooth, glabrous. Luster, front surface: Dull sheen. Luster, rear surface: Glaucous. Color, front surface: Distal open portion: Close to 155A to 155C; venation, close to 160D faintly tinged with close to 147D; with development, color becoming closer to 199A and N199B. Proximal closed portion: Close to 147C to 147D; towards the base, darkly flushed with close to N186D; color does not change with development. Color, rear surface: Distal open portion: Close to 158A marbled with close to 155C; towards the apex, close to 145B to 145C; areas adjacent to venation, close to 145B to 145C; color does not change with development. Proximal closed portion: Close to 147B variously streaked and marbled with close to 191A and 191B; venation, close to 146A to 146B; color does not change with development.

*Spadix*.—Length: About 7.9 cm. Length, male flower zone: About 5 cm. Length, sterile zone: About 9 mm.

Length, female flower zone: About 2 cm. Diameter, male flower zone: About 1 cm. Diameter, sterile flower zone: About 5.5 mm. Diameter, female flower zone: About 9 mm. Shape: Columnar to spindle-shaped. Apex: Bluntly acute. Base: Obtuse. Aspect: Upright. Color, mature, male zone: Close to 158A. Color, mature, sterile zone: Close to 158D. Color, mature, female zone: Close to 8B, 8D and 155D. Male flowers: Quantity per spadix: About 200. Shape: Obovate. Height: About 3 mm. Diameter: About 3 mm. Pollen amount: Moderate. Pollen color: Close to 4C. Female flowers: Quantity per spadix: About 150. Shape: Obovate. Height: About 3 mm. Diameter: About 2 mm. Stigma color: Close to 8B and 8D. Ovary color: Close to 155D.

*Scape*.—Length: About 25.5 cm. Diameter: About 6 mm. Strength: Sturdy; flexible. Aspect: Mostly erect. Texture: Smooth, glabrous; glaucous. Color, just below spathe: Close to 147C faintly streaked and stippled with close to 200D. Color, overall: Close to 196C tinged with close to 147C to 147D and sparsely stippled and streaked with close to 200D.

*Seeds and fruits*.—To date, seed and fruit development have not been observed on plants of the new *Caladium*.

Disease & pest tolerance: Plants of the new *Caladium* have been observed to have above average tolerance to *Xanthomonas* Leaf Spot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11.

It is claimed:

1. A new and distinct *Caladium* plant named 'Carousel' as illustrated and described.

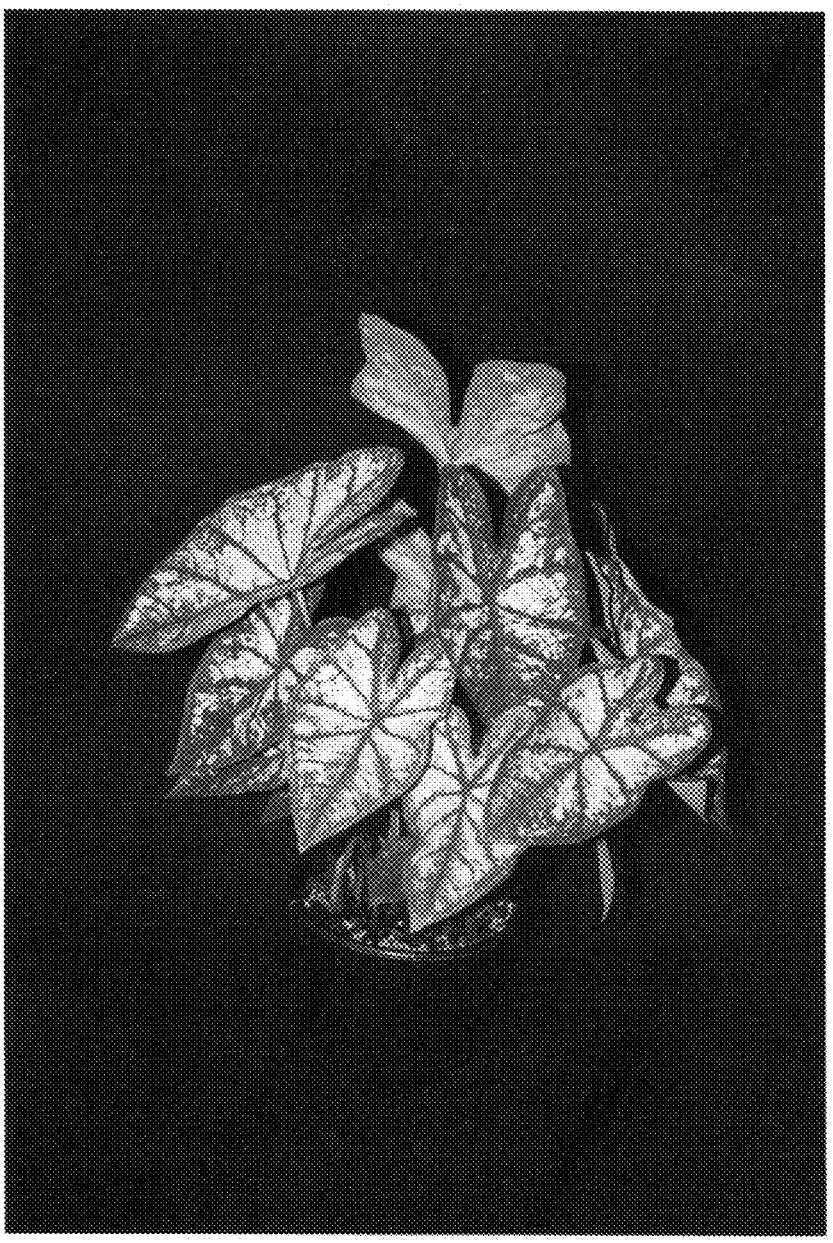

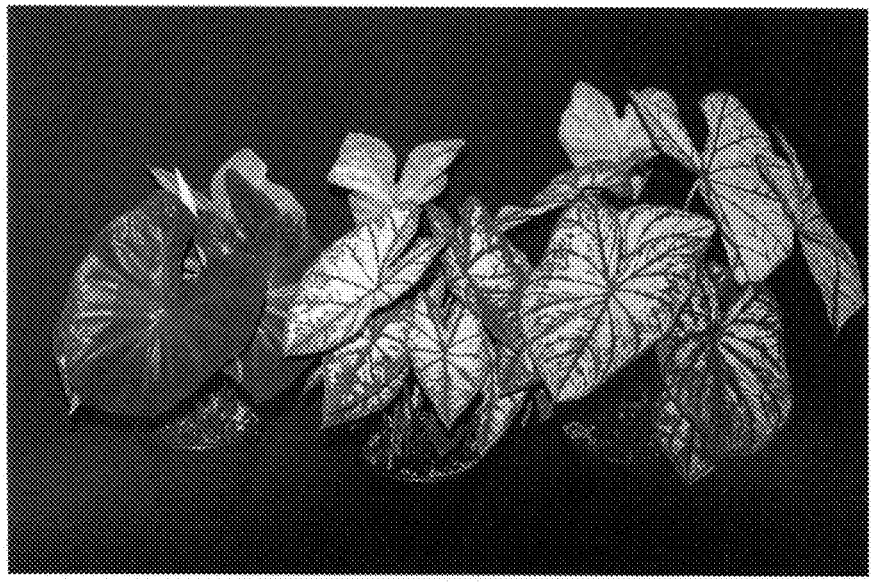
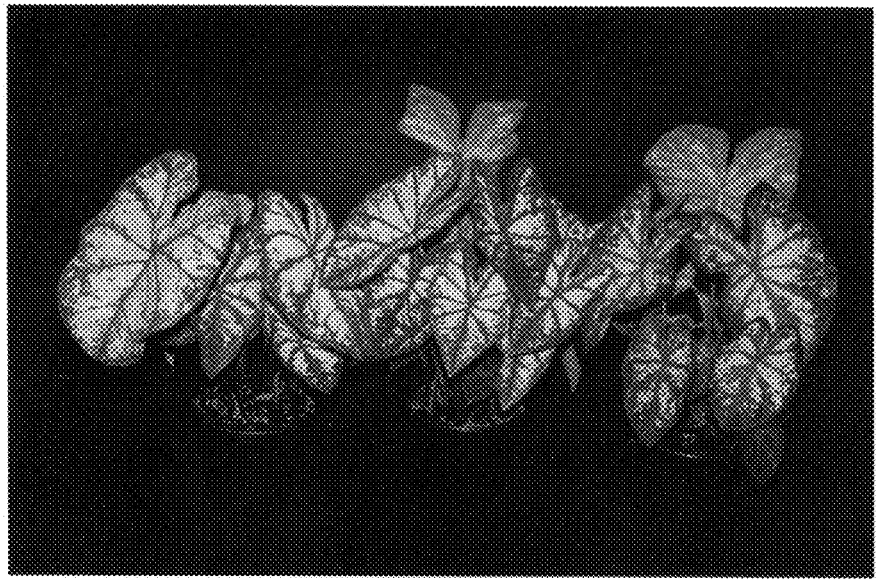

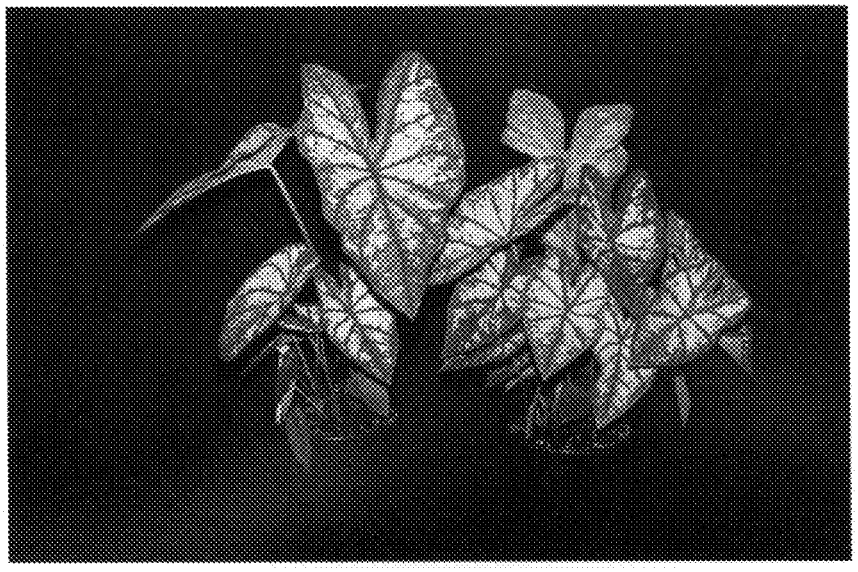
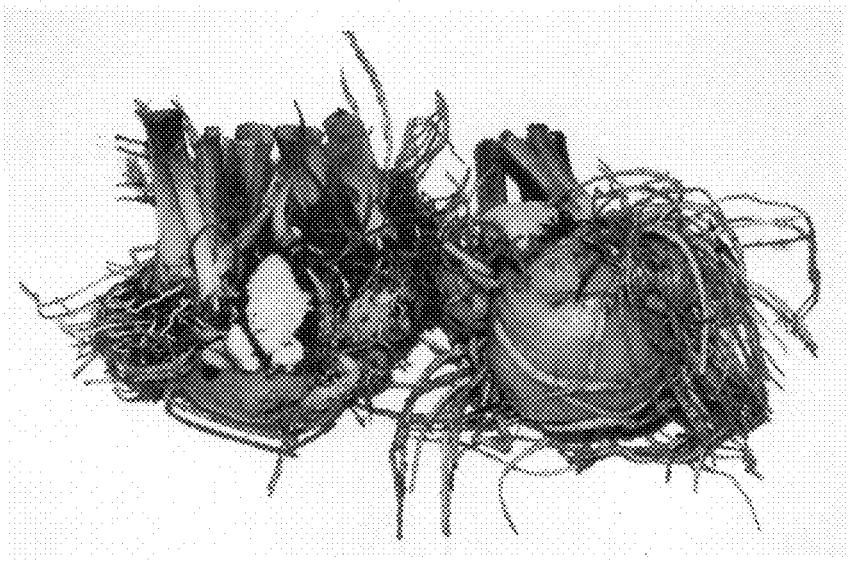

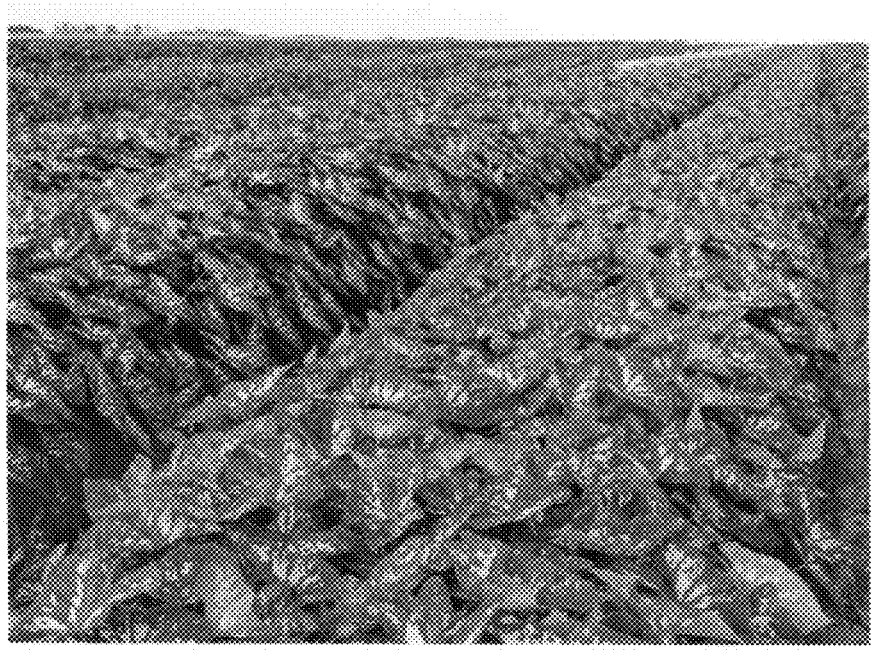
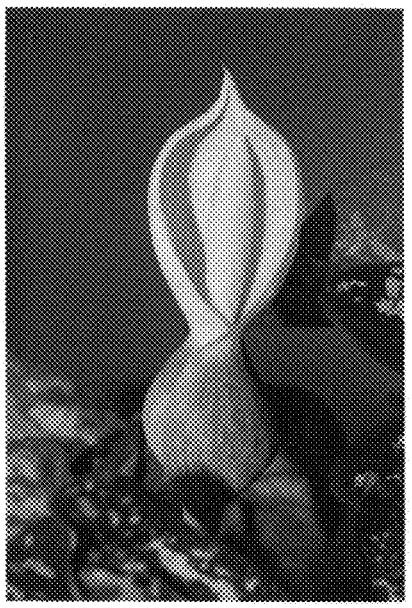

* * * * *